US007026161B2

(12) United States Patent
Park (10) Patent No.: US 7,026,161 B2
(45) Date of Patent: Apr. 11, 2006

(54) *LACTOBACILLUS* SP. STRAIN AND USE THEREOF (75) Inventor: Soon-Duck Park, Seoul (KR)

(73) Assignee: Sesang Life Science, Inc., Keyang Ki Do (KR)

( * ) Notice: Subject to any disclaimer, the term of this patent is extended or adjusted under 35 U.S.C. 154(b) by 20 days.

(21) Appl. No.: 10/500,348

(22) PCT Filed: May 15, 2002

(86) PCT No.: PCT/KR02/00914

§ 371 (c)(1),
(2), (4) Date: Jun. 25, 2004

(87) PCT Pub. No.: WO03/055987

PCT Pub. Date: Jul. 10, 2003

(65) Prior Publication Data

US 2005/0019894 A1    Jan. 27, 2005

(30) Foreign Application Priority Data

Dec. 27, 2001    (KR) .................. 10-2001-0085666

(51) Int. Cl.
*C12N 1/20*   (2006.01)
*A61K 39/02*  (2006.01)
*A61K 45/00*  (2006.01)

(52) U.S. Cl. .............. 435/252.9; 435/853; 424/234.1
(58) Field of Classification Search ........... 435/252.9, 435/853; 424/234.1
See application file for complete search history.

(56) References Cited

FOREIGN PATENT DOCUMENTS

| EP | 0 861 905 A2 | 9/1998 |
| EP | 0 861 905 A3 | 5/2002 |
| KR | 000047065 A | 7/2000 |
| WO | WO/99/29833 | 6/1999 |

OTHER PUBLICATIONS

Martha I. Alvarez-Olmos, et al., Probiotic Agents and Infectious Diseases: A Modern Perspective on a Traditional Therapy, Probiotic Agents and Infectious Diseases, CID 2001:32 (Jun. 1).

*Primary Examiner*—Robert A. Wax
*Assistant Examiner*—Rosanne Kosson
(74) *Attorney, Agent, or Firm*—Lucas & Mercanti, LLP (57) ABSTRACT

The present invention relates a novel *Lactobacillus* sp. strain and use thereof. More specifically, the present invention relates to a novel *Lactobacillus* sp. strain, *Lactobacillus paracasei*, isolated and identified from Kimchi fermentation liquid and uses thereof as probiotics, feeding additive, deodorizing agent and food additive. *Lactobacillus paracasei* of the present invention has good acid-resistance, bile acid-resistance and stability in the human body, has pathogenic bacteria inhibiting activity, increases numbers of beneficial bacteria by changing intestinal microflora and decreases diarrhea incidence, deodorizes offensive odor, and has effectes of softening and deodorizing in meat and fish.

9 Claims, 1 Drawing Sheet

FIG. 1

SEQUENCE LISTING

<160> NUMBER OF SEQ ID NOS: 1

<210> SEQ ID NO 1
<211> LENGTH: 1525
<212> TYPE: DNA
<213> ORGANISM: Lactobacillus paracase viro-01
<220> FEATURE:
<221> NAME/KEY: rRNA
<222> LOCATION: (1)..(1525)
<223> OTHER INFORMATION: Sequence of 16S rRNA

<400> SEQUENCE: 1

```
catgaacgct ggcggcgtgc ctaatacatg caagtcgaac gagttctcgt tgatgatcgg      60
tgcttgcacc gagattcaac atggaacgag tggcggacgg gtgagtaaca cgtgggtaac     120
ctgcccttaa gtgggggata acatttggaa acagatgcta ataccgcata gatccaagaa     180
ccgcatggtt cttggctgaa agatggcgta agctatcgct tttggatgga cccgcggcgt     240
attagctagt tggtgaggta atggctcacc aaggcgatga tacgtagccg aactgagagg     300
ttgatcggcc acattgggac tgagacacgg cccaaactcc tacgggaggc agcagtaggg     360
aatcttccac aatggacgca agtctgatgg agcaacgccg cgtgagtgaa gaaggctttc     420
gggtcgtaaa actctgttgt tgaagaagaa tggtcggcag agtaactgtt gtcggcgtga     480
cggtatccaa ccagaaagcc acggctaact acgtgccagc agccgcggta atacgtaggt     540
ggcaagcgtt atccggattt attgggcgta aagcgagcgc aggcggtttt ttaagtctga     600
tgtgaaagcc ctcggcttaa ccgaggaagc gcatcggaaa ctgggaaact tgagtgcaga     660
agaggacagt ggaactccat gtgtagcggt gaaatgcgta gatatatgga agaacaccag     720
tggcgaaggc ggctgtctgg tctgtaactg acgctgaggc tcgaaagcat gggtagcgaa     780
caggattaga taccctggta gtccatgccg taaacgatga atgctaggtg ttggagggtt     840
tccgcccttc agtgccgcag ctaacgcatt aagcattccg cctggggagt acgaccgcaa     900
ggttgaaact caaaggaatt gacgggggcc cgcacaagcg gtggagcatg tggtttaatt     960
cgaagcaacg cgaagaagct taccaggtct tgacatcttt tgatcacccg agagatcagg    1020 tttcccttc gggggcaaaa tgacaggtgg tgcatggttg tcgtcagctc gtgtcgtgag    1080
atgttgggtt aagtcccgca acgagcgcaa cccttatgac tagttgccag catttagttg    1140
ggcactctag taagactgcc ggtgacaaac cggaggaagg tggggatgac gtcaaatcat    1200
catgcccctt atgacctggg ctacacacgt gctacaatgg atggtacaac gagttgcgag    1260
accgcgaggt caagctaatc tcttaaagcc attctcagtt cggactgtag ctgcaactc     1320 gcctacacga agtcggaatc gctagtaatc gcggatcagc acgccgcggt gaatacgttc    1380
ccgggccttg tacaccgcc ccgtcacacc atgagagttt gtaacacccg aagccggtgg    1440 cgtaacccctt ttagggagcg agccgtctaa ggtgggacaa atgattaggg tgaagtcgta    1500
acaaggtagc cgtaggagaa cctgc                                         1525
```

LACTOBACILLUS SP. STRAIN AND USE THEREOF

This patent application claims the benefit of priority from Korean Patent Application No. 10-2001-0085666 filed Dec. 27, 2001 through PCT Application Serial No. PCT/KR2002/00914 filed May 15, 2002, the contents of each of which are incorporated herein by reference.

TECHNICAL FIELD

The present invention relates to a novel *Lactobacillus* sp. strain and uses thereof. More specifically, the present invention relates to a novel *Lactobacillus* sp. strain, *Lactobacillus paracasei*, isolated and identified from Kimchi fermentation liquid, and uses thereof as probiotics, feed additive, deodorizing agent and food additive.

BACKGROUND OF THE INVENTION

Kimchi is a fermented food unique to Korea, primarily comprised of Chinese cabbage or white radish, made by adding various spices to the main vegetable ingredient and then fermenting them. Studying of microorganisms involved in the Kimchi fermentation process first began in the 1930's. Lactic acid bacteria such as the *Lactobacillus* sp., *Pediococcus* sp. and *Leuconostoc* sp. strains, for example, are primarily representative.

Among these, *Lactobacillus* sp. strains are either homogeneous or heterogeneous fermenting *Lactic Acid Bacillus*, which can be usually found in animal and human intestinal tracts and are used in the fermentation process of dairy foods and vegetables. *Lactobacillus* sp. strains maintain intestinal pH to acidic states, thereby inhibiting the growth of harmful bacteria such as *E. coli* or Clostridium, alleviating diarrhea and constipation, functioning immunologically, as well as assisting vitamin synthesis, anti-cancer action and serum cholesterol reduction, etc. It is known that acidophillin, produced by *Lactic Acid Bacillus*, inhibits the growth of *Shigella, Salmonella, Staphylococcus, E. coli*, etc. Also, acidophillin inhibits the proliferation of diarrhea-causing bacteria and normalizes intestinal microflora, thereby stopping diarrhea.

Recently, studies to develop probiotics and animal feed by using such characteristics of *Lactobacillus* sp. strains have been actively underway. The bacterial diarrhea of domestic and farm animals causes reduced growth rates and death. Thus, to prevent this condition and increase livestock productivity, adding antibiotics to animal feed has become a common practice. However, due to the advent of antibiotic-resistant bacteria and the problems associated with residual antibiotics in livestock products, policies that regulate the use of antibiotics in animal feed, and pursue organic feeding and breeding methods of animals, are gaining approval. Currently, the use of probiotics is actively recommended as an alternative for antibiotic use.

European Patent Publication No. 0861905 disclosed a novel *Lactobacillus* sp. strain, and a pharmaceutical composition and dairy product(s) for treating gastrointestinal diseases comprising the same. WO Publication No. 99/29833 disclosed *Lactobacillus paracasei*, a strain that is useful as probiotics and a natural drug applicable to food products. KR Patent Laid-Open Publication No. 1998–78353 disclosed a novel acid-resistant *Lactobacillus* sp. strain having harmful bacteria-inhibiting activity and farm animal probiotics comprising the same.

SUMMARY OF THE INVENTION

The present inventors have isolated and identified a novel *Lactobacillus* sp. strain having superior acid-resistance property, bile acid-resistance property and harmful bacteria-inhibiting activity from Kimchi fermentation liquid. The present microorganism is non-toxic to humans and therefore very safe, and the said microorganism or fermentation liquid can be used as probiotics for preventing or treating gastrointestinal-associated diseases of animals, feed additive, deodorizing agent, and food additive.

Therefore, the present invention provides a novel *Lactobacillus* sp. strain isolated from Kimchi fermentation liquid.

The present invention provides probiotics for preventing or treating animal intestinal diseases, characterized by the said *Lactobacillus* sp. strain or fermentation liquid thereof.

The present invention provides a feed additive characterized by the above said *Lactobacillus* sp. strain or fermentation liquid thereof.

The present invention provides a deodorizing agent characterized by the above said *Lactobacillus* sp. strain or fermentation liquid thereof.

The present invention provides a food additive characterized by the above said *Lactobacillus* sp. strain or fermentation liquid thereof.

DETAILED DESCRIPTION

The present invention provides a novel *Lactobacillus* sp. strain isolated from Kimchi fermentation liquid. The inventive *Lactobacillus* sp. strain is *Lactobacillus paracasei* viro-01, which has superior acid-resistance property, bile acid-resistance property, harmful microorganism-inhibiting activity and safety for use in the human body.

*Lactobacillus* sp. strains are widely present in nature and they anaerobically metabolizes carbohydrates to produce lactic acid. Generally, it is known that when lactic acid bacteria such as *Lactobacillus* sp. strain are added directly or indirectly to food products, their metabolic product, lactic acid, improves a shelf life, flavor and texture of the food product. Also, lactic acid bacteria ingested along with fermented foods enter the intestine and adhere to intestinal epithelial cells, thereby providing beneficial effects including a pathogenic microorganism-inhibiting and antagonizing action, enhancement of immunoactivity, decrease of cancer incidence, and decrease of tumorigenic enzyme activity etc. to a host animal. Therefore, in Western and Oriental countries, lactic acid bacteria are used in processing of dairy products, meat products, pickled vegetables and various salted and pickled seafoods, as well as being used as probiotics. At this time, in order to use lactic acid bacteria as probiotics, said bacteria have to be gastric acid- or bile acid-resistant so as to be high in intestinal delivery rate, and they have to adsorb and anchor to intestinal epithelial cells or mucous membranes, and preferably secrete anti-bacterial substance to suppress harmful bacteria, thus stabilizing the intestinal environment and preventing intestinal anchoring by harmful bacteria, and they also have to be safe for use in foodstuffs. The present inventive *Lactobacillus* sp. strain,

*Lactobacillus paracasei* viro-01 is a novel microorganism having all the above said properties.

Isolation and identification of *Lactobacillus* sp. strain of the present invention were carried out by following method. First, Kimchi fermentation liquid was serially diluted and cultivated in selection medium for lactic acid bacteria.

After isolating only lactic acid bacteria, and among these, selecting Gram positive *bacillus* strains, cultivation was performed in *Lactobacillus*-selective medium to isolate *Lactobacillus* sp. strains. Out of these, microorganisms having high acid productivity were finally isolated. Identification of said isolated microorganisms may be carried out according to the Bergey's manual taxonomy and criteria, based on their morphological, growth and physiological properties.

For example, physiological properties such as Gram staining, oxygen-demanding property, auxotrophy, assimilation property, metabolites, enzymatic reaction or antibiotic-resistance may be used. And also, there can be used DNA sequence analysis, 16S RNA structure analysis, cell wall constituent, quinone type of electron transfer system, chemical classification methods based on fatty acid compositon of bacterial mass(MIDI) and immunological methods, for this purpose.

The present inventors analysed and identified the glucose consumption mode and the base sequence of 16S rRNA for the isolated *Lactobacillus* sp. strain and deposited the said microorganism with Korean Collection for Type Cultures, 52, Oun-dong, Yusong-ku, Taejon, Korea, an International Depository Authority under the Budapest Treaty, under Accession No. KCTC 10132BP, on Dec. 3, of 2001. Any restriction on the release of this strain to the public will be irrevocably removed upon the issuance of a patent.

*Lactobacillus paracasei* viro-01(KCTC-10132BP) according to the present invention has the following characteristics.

1. This microorganism survives under the low pH stress and has strong resistance to bile acid. Specifically, *Lactobacillus paracasei* viro-01 of the present invention has an ability to survive under pH of less than 3.0 and 0.5% of Oxgall.

2. *Lactobacillus paracasei* viro-01 of the present invention has the harmful microorganism-inhibiting activity. Said harmful microorganisms include, but are not limited to, *E. coli, E. coli* O157, *Staphylococcus aureus, Vibrio parahaemolyticus, Salmonella typhi, Pseudomonas aeruginosa, Bacillus cereus* and *Bacillus subtilis*.

3. *Lactobacillus paracasei* viro-01 of the present invention has a wide antibiotic-resistance. These antibiotics include, but are not limited to, Cephalexin, Flumequine, Furazolidone, Spectinomycin, Kanamycin, Gentamycin and Neomycin.

4. *Lactobacillus paracasei* viro-01 of the present invention has safety in human body. Fermentation liquid of *Lactobacillus paracasei* viro-01 of the present invention has a unique color and flavor, has no unpleasant taste or odor, and is *E. coli* group-negative. Also, tar pigments and remaining noxious substance(Pb, Cd, Hg, As, Cr16) was not detected, thus being safe for use in the human body.

*Lactobacillus paracasei* viro-01 of the present invention can be cultivated in mass by conventional culturing methods of *Lactobacillus* sp. strain. As a culture medium, the medium composed of carbon source, nitrogen source, vitamins and minerals can be used, for example MRS broth(de Man-Rogosa-Sharp broth) and milk-added broth. Microorganisms can be cultivated under the conventional conditions for cultivation of lactic acid bacteria, for example, at a temperature of 15–45° C., for 10–40 hours. In order to remove media from culture and recover only concentrated bacterial mass, a centrifugation or filtration process can be performed, if desired, by those skilled in the art. Concentrated bacterial mass can be frozen or lyophilized by conventional methods to preserve it without loss of activity.

A fermentation liquid of lactic acid bacteria can be produced by using the microorganism of the present invention. To achieve this, *Lactobacillus paracasei* viro-01 of the present invention can be inoculated into any fruit juice and cultivated anaerobically, for example. Said fruit juice refers to liquid prepared by crushing and pressing any fruit, and there is no particular limitation to kinds of fruit juice. Example of juice which can be used include, but are not limited to, apple, orange, grape and jujube juice etc. Said fruit juice was diluted with purified water and adjusted to a brix degree of 1 to 15%. Into this diluted fruit juice was inoculated *Lactobacillus paracasei* viro-01 of the present invention in concentration of 1 to 5% (v/v) and incubated at 15–45° C., for 10 to 80 hours. pH was monitored regularly, and when it reached a range of 2.0 to 4.0, more preferably 2.8 to 3.5, the culture was transferred to an incubator at 20 to 40° C. for 5 to 10 days, during which time pH adjusted to a value of 2.0 to 5.0, preferably 3.0 to 4.0.

At that time, the fermentation was aerated for 1 hour about every 24 hours.

After completing fermentation process, fermentation liquid was recovered.

Following the recovery of fermentation liquid, one to ten volumes, more preferably one to five volumes of purified water was added to remaining lactic acid bacteria mass and precipitates in an incubator and then the incubation was continued by the same method as above. Then, purified water was added to dilute the fermentation liquid 1 to 10 times, preferably 1 to 5 times and the fermentation was aged.

Preferably, lactic acid bacteria of the present invention can be stored following concentration, centrifugation or filtration and then subsequent stabilization, lyophilization, spray drying or encapsulation of culture or fermentation liquid. For example, culture or fermentation liquid can be concentrated to remove liquid by centrifugation or filtration in the first stage, or preferably can be directly stabilized from fermentation liquid while adding filler or carrier, e.g. Aluminium silicate, diatomaceous earth, carbohydrates, sugar alcohol, starch, milk and whey powder, protein hydrolysate material, yeast and PVPP. By addition of these carriers or fillers, it is possible to obtain the solid products in a subsequent stabilization step, particularly in lyophilization, spray drying and encapsulation steps of pelletized matters.

The present invention provides probiotics for preventing or treating intestinal diseases of animals, comprising *Lactobacillus paracasei* viro-01 of the present invention or fermentation liquids thereof.

Term "animal" used herein, refers to mammals including a human, and preferably includes domestic and farm animal such as cattle, horse, pig etc. The term "intestinal disease" used herein includes, but is not limited to, e.g. infectious diarrhea caused by pathogenic microorganisms such as *E. coli, Salmonella*, Clostridium, etc., gastroenteritis, inflammatory intestinal disease, neurological intestinitis syndrome, overgrowth of small intestinal microorganisms, intestinal feeding diarrhea.

Term "Probiotics" used herein, means preparation of live bacteria, i.e. microorganisms which can remain and survive in the gastrointestinal tract when they are ingested by a human or animal, and which can provide prevention or treatment of diseases. Specifically, it is a medicinal product or animal medicament made by formulating said microorganism in a live state. Generally, probiotics have an effect to treat and ameliorate the various diseases caused by abnormal growth of intestinal bacterial microflora and when administered to a human and animal, they localize and settle on the wall of the digestive tract to prevent harmful bacteria from anchoring, and produce lactic acid to thus lower the intestinal pH to prevent the proliferation of harmful bacteria. Also, probiotics produce bacteriocin and peroxides in vivo to inhibit proliferation of pathogenic bacteria and have an effect to promote action of intestinal villi responsible for nutrient absorption. In addition, they produce substances which assist the absorption and use of nutrients, improve the demanding rate of feed in livestock and also produce substances which neutralize toxic substances produced by pathogenic bacteria.

The above-said probiotics of the present invention comprise Lactobacillus paracasei viro-01 as an active ingredient and can be administered in the form of a mixture comprising said bacteria and pharmaceutically acceptable carriers by various formulations and methods.

An effective amount of *Lactobacillus paracasei* viro-01 means preferably more than $10^7$ cells/g, more preferably, $10^7$ cells/g to $10^9$ cells/g. There can be used a binding agent, excipient, disintegrating agent, lubricating agent, coating agent, solubilizer, dispersant, stabilizer, suspending agent, pigment and fragrance as a carrier.

The binding agent includes, but is not limited to, polysaccharides such as dextrin, sodium alginate, karageenan, guar gum, acacia, agar etc., naturally-occurring macromolecular substances such as tragacanth, gelatin, gluten etc., cellulosic derivatives such as hydroxypropylcellulose, methylcellulose, hydroxypropylmethylcellulose, ethylcellulose, hydroxypropylethylcellulose, sodium carboxymethylcellulose etc., and synthetic polymers such as polyvinylpyrolidone, polyvinyl alcohol, polyvinylacetate, polyethyleneglycol, polyacrylic acid, polymethacrylic acid and vinyl acetate resins.

The excipient includes sugar such as sucrose, lactose, mannitol, glucose etc. and starch such as corn starch, potato starch, rice starch, partially-pregelatinized starch etc.

The disintegrating agent includes cellulosic derivatives such as carboxymethylcellulose, calcium carboxymethylcellulose, lower-substituted hydroxypropylcellulose etc., and starch such as sodium carboxymethyl starch, hydroxypropyl starch, corn starch, potato starch, rice starch and partially-pregelatinized starch etc.

The lubricating agent includes talc, stearic acid, calcium stearate, magnesium stearate, colloidal silica, hydrous silicon dioxide, various kinds of wax and hydrogenated oil etc.

The coating agent includes water-insoluble polymers such as dimethylaminoethylmethacrylate-methacrylic acid copolymer, polyvinylacetaldiethylaminoacetate, ethylacrylate-methacrylic acid copolymer, ethylacrylate-methylmethacrylate-chlorotrimethylammoniumethylmethacrylate copolymer, ethylcellulose etc., tonic copolymer such as methacrylic acid-ethylacrylate copolymer, hydroxypropylmethylcellulose phthalate, hydroxypropylmethylcellulose acetyl succinate etc., and water-soluble polymer such as methylcellulose, hydroxypropylmethylcellulose, polyvinylpyrolidone, polyethyleneglycol etc.

Probiotics of the present invention can be prepared in the form of tablet, troche, capsule, elixir, suspension, syrup, wafer, powder, granule etc. by mixing them with the above said carriers. It is preferably administered via oral route. In addition, a pharmaceutical composition can be prepared in the various forms by conventional techniques.

Dosage can be suitably determined depending on the rate of in vivo absorption, inactivation and excretion of active ingredient, age, sex, condition of patients and severity of the disease to be treated.

The present invention provides a feed additive comprising Lactobacillus paracasei viro-01 of the present invention or fermentation liquid thereof. The feed additive of the present invention has an effect to increase useful lactic acid bacteria microflora in animal intestine, decrease the incidence of diarrhea, and increase the growth rate of the animal.

The feed additive of the present invention comprises lactic acid bacteria of the present invention or fermentation liquid thereof. Preferably, it comprises the lactic acid bacteria-fruit juice fermentation liquid prepared by inoculating the said lactic acid bacteria into fruit juice or the fermentation liquid prepared by first recovering the said lactic acid bacteria-fruit juice fermentation liquid and adding a certain amount of water to remaining bacterial mass and precipitates to dilute them, and then re-fermenting them. More preferably, it is possible to use essentially pure lactic acid bacteria culture, if desired, by adding the carrier material to said culture, and lyophilizing, spray drying, encapsulating or pelletizing it. The feed additive according to the present invention comprises the lactic acid bacteria of the present invention or the lactic acid bacteria culture prepared by the method of the present invention in amount of ranging from $10^5$ to $10^{12}$ cells/kg, preferably $10^7$ to $10^9$ cells/kg.

The feed additive according to the present invention may further comprise carrier and/or filler to enhance its physiological activity. An example of the said carrier and/or filler includes, but is not limited to, aluminium silicate, diatomaceous earth, carbohydrate, sugar alcohol, starch, milk and whey powder, protein hydrolyzate material, yeast and PVPP.

Feed additive according to the present invention can be mixed in feed during the conventional feed manufacturing process or can be mixed into animal feed in solid or liquid form when supplying feed to an animal. Said animal feed includes, but is not limited to, for example fermentation feed, compound feed, pelletized form and silage form. Fermentation feed can be prepared by adding feed additive of the present invention to organic materials and fermenting them.

Compound feed can be prepared by mixing many kinds of conventional and general feed with a feed additive of the present invention. For example, the feed additive of the present invention can be prepared by mixing more than two kinds of commercially available feed raw material in a given ratio to produce compound feed, and mixing the said compound feed with the *Lactobacillus paracasei* viro-01 culture of the present invention in an amount of ranging from 1 to 2 kg, based on 1 ton of compound feed. The pelletized form of said compound feed etc. can be prepared by applying heat and pressure to said compound feed in a pelletizer. Silage can be prepared by adding forage crops feed to feed additive of the present invention and fermenting them.

The present inventors confirmed that adding lactic acid bacteria fermentation liquid of the present invention to drinking water and supplying it to parent pigs and progeny pigs decreased death rate and diarrhea incidence and increased the rate of weight gain(Example 5). And also, upon determining the changes to the enteric microorganisms population in weaned piglets to which lactic acid bacteria fermentation liquid of the present invention was supplied, the number of pathogenic microorganism, *Salmonella* and *E. coli* decreased and the number of lactic acid bacteria significantly increased(Example 6).

Further, the present invention provides a deodorizing agent comprising *Lactobacillus paracasei* viro-01 or fermentation liquid thereof. The term "Deodorizing agent" used herein means an agent capable of removing offensive odors, and in general, the deodorizing mechanism includes masking and odor-neutralization, acid-alkali neutralization, chemical mechanisms by chemical reaction, physical mechanisms by adsorbent activated charcoal, plant extracts and biological mechanisms by enzymatic degradation etc. The deodorizing agent of the present invention comprises lactic acid bacteria of the present invention or fermentation liquid thereof and thus functions to remove odor by a biological mechanism. Preferably, the deodorizing agent of the present invention comprises lactic acid bacteria-fruit juice fermentation liquid prepared by inoculating lactic acid bacteria of the present invention into fruit juice, or it comprises the fermentation liquid prepared by first recovering the said lactic acid bacteria-fruit juice fermentation liquid and then adding a certain amount of water to the remaining bacterial mass and precipitates to make them dilute and re-fermenting them. The deodorizing agent of the present invention can be provided in the form of liquid deodorizing agent consisting of the said lactic acid bacteria fermentation liquid and purified water, or in the form of powdered deodorizing agent consisting of the said liquid deodorizing agent and microorganism carrier. There can be used zeolite, activated charcoal, wollastonite, pearlite, diatomaceous earth and porous ceramic etc. as the above carriers. Preferably, deodorizing agent of the present invention can be prepared by filtering lactic acid bacteria fruit juice fermentation liquid and diluting it with purified water and adding lactic acid bacteria to a concentration ranging from about $1.0 \times 10^5$ to $1.0 \times 10^9$ cells/ml.

In order to improve palatability, deodorizing agent of the present invention can provide an odorless deodorizing agent with or without added fragrance. The fragrance includes for example, fruit aroma such as apple, papaya, lemon, orange, vanila aroma etc., flower aroma such as rose, jasmin, lilac, freesia etc., perfume such as Envy, Cooling, Perfecto, Floral, Osmanthus(brand name of perfume) etc., and plant aroma such as pinetree, cucumber, mint etc.

The deodorizing agent of the present invention can be used in the form of the spray container or can be prepared into any formulation according to intended use of the deodorizing agent. For example, the deodorizing agent of the present invention can be filled and used in spray container in a certain amount (i.e., for personal use: 90 ml, for commercial use: 500 ml) and it can be directly sprayed into the air or directly applied to an odor source.

The deodorizing agent of the present invention has a potent deodorizing effect, and thus can be applied for broad and various purposes. In other words, it is effective for deodorizing of closed narrow spaces (for example, refrigerator, bathroom), as well as for deodorizing of open spaces. The deodorizing agent of the present invention is useful for removal of offensive odors in wide and various situations, for example the removal of, but not limited to, odor of refrigerator, domestic odors of a human, animal, tobacco etc., odor of household or public toilets, odor of domestic refuse heaps or animal excretions, as well as for removal of odors of poultry farms, piggery and waste incineration yard which occasionally cause problems associated with environmental hygiene. Also, because the deodorizing agent of the present invention consists of ingredients which are not harmful to the human body, even if it comes in contact with the human body, farm animals and plants, it doesn't display toxicity to them.

Further, *Lactobacillus paracasei* viro-01 of the present invention or fermentation liquid thereof can be used for deodorizing of food. Therefore, the present invention provides a food composition comprising *Lactobacillus paracasei* viro-01 or fermentation liquid thereof. The food composition of the present invention comprises lactic acid bacteria of the present invention or fermentation liquid thereof, and preferably lactic acid bacteria fruit juice fermentation liquid prepared by inoculating fruit juice with lactic acid bacteria of the present invention, or it comprises the fermentation liquid prepared by first recovering the said lactic acid bacteria-fruit juice fermentation liquid and adding a certain amount of water to remaining bacterial mass and precipitates to dilute them and then re-fermenting them. The food composition of the present invention can be prepared by filtering said lactic acid bacteria fruit juice fermentation liquid and then diluting it with purified water 10 to 100 times. The food composition of the present invention has softening action and an effect of decreasing offensive smells of meat and fish.

Because the said *Lactobacillus paracasei* viro-01 has an anti-bacterial action versus harmful pathogenic bacteria, it inhibits bacterial proliferation in food and decreases the risk of food poisoning. For example, the food composition of the present invention has an effect to decrease offensive smell and soften meat by addition of the said composition to cooked food containing meat such as steamed pig rib, panbroiled pork, broiled beef, steamed beef rib, chicken broth, fried chicken or to cooked food including fish such as broiled mackerel and spiced fish soups.

Now, the present invention was explained in detail with reference to the following examples, which are provided only for the purpose of illustrating, and are not intended to limit, the present invention.

EXAMPLE 1

Isolation and identification of *Lactobacillus* sp. strain 1-1) Isolation of *Lactobacillus* sp. Strain from Kimchi Chinese cabbage Kimchi was made and fermented at 25° C. for 20 days(pH 4.0±0.2) by traditional method. 1 ml of said fermented Kimchi liquid was serially diluted with sterilized physiological solution to a dilution factor of $10^1$ to $10^7$ and then 0.1 ml of each dilution was inoculated onto BHI(Brain Heart Infusion, Difco, USA) and incubated at 37° C. for 72 hours. Cultured bacterial mass was cultivated in BCP(Brom Cresol Purple) agar medium, a medium for detecting lactic acid whereby color changes from purple to yellow by lactic acid production, and bacterial strains having good lactic acid production were primarily isolated.

The isolated bacterial strains were Gram stained and observed under microscope to select *bacillus* strains. After selecting Gram positive *bacillus* type microorganisms, they were incubated at 30° C. in an incubator for 48 hours using LBS(*Lactobacillus*-selective) medium to isolate only *Lactobacillus* sp. strains.

The number of firstly isolated strain was 30, among these we selected 10 strains, which were putative *bacillus* sp. strains. These bacterial strains were passaged on BHI medium.

1-2) Identification of isolated strain

The present inventors inoculated sterilized fruit juice with bacterial strains isolated from the above example 1-1, fermented them and selected the bacterial strains which were able to reduce pH of fermentation liquid below 3.0 by themselves. Selected bacterial strains were analyzed for consumption mode of substrate using API CHL Kit(Bio Merioux Corp.) according to the Manufacturer's instructions. Analysis results by API CHL Kit are shown in Table I below.

In order to allow more precise identification of the bacterial strain according to the present invention, we requested for Probionic Corp.(Korean Biotechnology Institute, Daejeon city, Republic Of Korea) to sequence the 16S rRNA gene from genomic DNA of the said strain, which was known to be diagnostic for identification of said strain.

Figure 1:
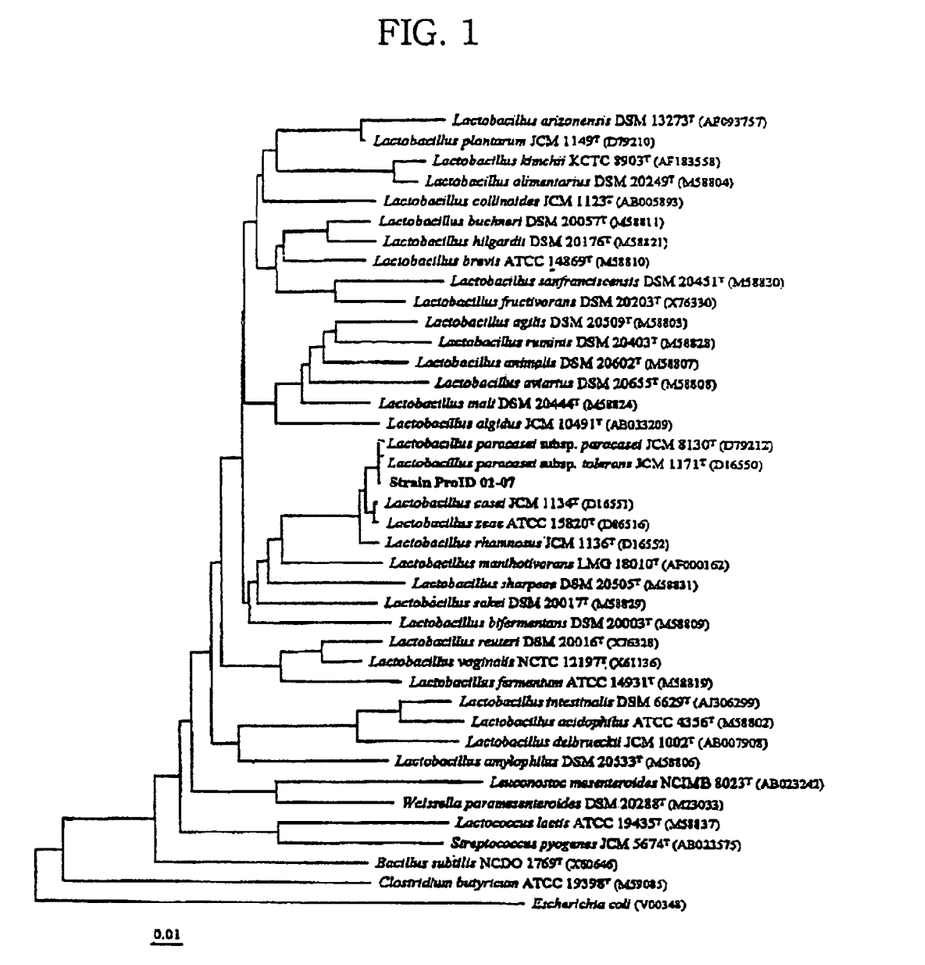
FIG. 1 represents a phylogenic classification based on 16S rRNA sequence of *Lactobacillus paracasei* viro-01 of the present invention (scale bar means 0.01% substitution of the nucleotide).

As a result, the bacterial strain of the present invention was identified as *Lactobacillus* sp., by molecular analysis based on 16S rRNA base sequence showing the most closely related species comprising *Lactobacillus paracasei, Lactobacillus casei, Lactobacillus zeae, Lactobacillus rhamnosus* (FIG. 1).

Especially, the present bacterial strain was identified as a strain showing the closest relationship to a standard strain of *Lactobacillus paracasei*, with sequence homology of 99.9% in 16S rRNA. The base sequence of the inventive bacterial strain is shown in SEQ. ID. No. 1. Consequently, the present inventors identified the bacterial strain as *Lactobacillus paracasei*, designated as *Lactobacillus paracasei* viro-01 and deposited the said microorganism with the Korean Collection for Type Cultures, 52, Oun-dong, Yusong-ku, Taejon, Korea, an International Depository Authority under the Budapest Treaty, under Accession No. KCTC 10132BP, on Dec. 3 of 2001.

TABLE 1

|  | Colony 1 | | Colony 2 | | |
|---|---|---|---|---|---|
| Contor | − | − | − | − | 0 |
| Glycerol | − | − | − | − | 1 |
| Erythritol | − | − | − | − | 2 |
| D-Arabinose | − | − | − | − | 3 |
| L-Arabinose | − | − | − | − | 4 |
| Ribose | + | + | + | − | 5 |
| D-Xylose | − | − | − | − | 6 |
| L-Xylose | − | − | − | − | 7 |
| Adonitol | + | + | + | − | 8 |
| β-Methyl-xyloside | − | − | − | − | 9 |
| Galactose | + | + | + | − | 10 |
| D-Glucose | + | + | + | − | 11 |
| D-Fructose | + | + | + | − | 12 |
| D-Mannose | + | + | + | − | 13 |
| L-Sorbose | − | − | + | − | 14 |
| Rhamnose | − | − | − | − | 15 |
| Dulsitol | − | − | − | − | 16 |
| Inositol | − | − | − | − | 17 |
| Manitol | + | + | + | − | 18 |
| Sorbitol | + | + | + | − | 19 |
| α-Methyl-D-mannoside | − | − | − | − | 20 |
| α-Methyl-D-glucoside | − | − | + | − | 21 |
| N-Acetyl glucosamine | + | + | + | − | 22 |
| Amygdalin | − | + | + | − | 23 |
| Arbutine | + | + | + | − | 24 |
| Esculine | + | + | + | − | 25 |
| Salicine | + | + | + | − | 26 |
| Cellobiose | + | + | + | − | 27 |
| Maltose | + | + | + | − | 28 |
| Lactose | − | − | − | − | 29 |
| Melibiose | − | − | − | − | 30 |
| Saccharose | − | + | − | + | 31 |
| Trehalose | + | + | + | − | 32 |
| Inuline | − | − | − | − | 33 |
| Melezitose | + | + | + | − | 34 |
| D-Raffinose | − | − | − | − | 35 |
| Amidon | − | − | − | − | 36 |
| Glycogen | − | − | − | − | 37 |
| Xylitol | − | − | − | − | 38 |
| β-Gentiobiose | − | + | + | − | 39 |
| D-Turanose | + | + | + | − | 40 |
| D-Lyxose | − | − | − | − | 41 |
| D-tagatose | + | + | + | − | 42 |

TABLE 1-continued

|  | Colony 1 | | Colony 2 | | |
|---|---|---|---|---|---|
| D-Fucose | − | − | − | − | 43 |
| L-Fucose | − | − | − | − | 44 |
| D-Arabitol | − | − | − | − | 45 |
| L-Arabitol | − | + | − | + | 46 |
| Gluconate | + | + | − | + | 47 |
| 2-aceto-gluconate | − | − | − | − | 48 |
| 5-aceto-gluconate | − | − | − | − | 49 |

EXAMPLE 2

Characterization of the *Lactobacillus paracasei* viro-01 of the present invention 2-1) Acid- and bile acid-resistance test

*Lactobacillus paracasei* viro-01 isolated from the above example 1 was suspended in 0.85% brine with pH 2.0 and 3.0 and incubated at 37° C. hourly. The culture was diluted decimally, smeared it MRS medium and the number of colonies was counted. As a result, all the test bacterial strains were grown, and it was confirmed from this that *Lactobacillus paracasei* viro-01 of the present invention possessed acid-resistance.

For the bile acid resistance test, bacterial strains were cultured in MRS liquid medium and smeared on MRS agar medium to which 0.2%, 0.3%, 0.5%, 0.7% and 1.0% of Oxgall(Difco) were added, incubated at 37° C. and then checked for growth. It was observed that all bacterial strains grew at Oxgall concentrations below 0.5%.

2-2) Determination of harmful microorganism-inhibiting activity

It was determined for harmful microorganism inhibitory activity of *Lactobacillus paracasei* viro-01 of the present invention. *Escherichia coli*(ATCC-25922), *Escherichia coli* O157, (ATCC-43895), *Staphylococcus aureus*(ATCC-25923), *Vibrio parahaemolyticus*(KCTC-2471), *Salmonella typhi*(KCTC-2424), and *Pseudomonas aeruginosa*(KCTC-1636) were grown in BHI liquid medium, as harmful microorganisms. For *Candida albicans*(KCTC-7965), SDB(Sabouraud Dextrose broth) was used as the medium.

After harmful microorganisms were inoculated into sterilized physiological saline solution and counted, *Lactobacillus paracasei* viro-01 of the present invention was added to concentration of 1% (v/v) and then left at room temperature.

After 30 sec, 2 min, 5 min and 24 hours, bacteria were counted.

As shown in Table 2, except for *Candida albicans*, significant bactericidal effects were observed. Especially, excellent effects for *Vibrio* sp., were observed, decreasing by 95.6% after 5 min. and completely killing all bacteria by 24 hrs.

Also, high bactericidal effects versus Salmonella typhi, *E. coli*, Staphylococcus aureus and Pseudomonas aeruginosa were observed.

TABLE 2

Harmful microorganism-inhibiting activity of
Lactobacillus paracasei of the present invention

| Bacteria | Initial | 30 s | 2 min | 5 min | 24 hrs |
|---|---|---|---|---|---|
| E. coli | $3.1 \times 10^5$ | $2.8 \times 10^5$ (9.7%) | $2.6 \times 10^5$ (16.1%) | $2.3 \times 10^5$ (25.8%) | 67.7% |
| E. coli O157 | $2.8 \times 10^5$ | $2.5 \times 10^5$ (10.7%) | $2.4 \times 10^5$ (14.3%) | $2.1 \times 10^5$ (25.0%) | 71.4% |
| Sta. aureus | $2.7 \times 10^5$ | $2.2 \times 10^5$ (18.5%) | $1.4 \times 10^5$ (48.1%) | $1.0 \times 10^5$ (63.0%) | 74.1% |
| V. parahaem | $1.1 \times 10^5$ | $7.5 \times 10^4$ (31.8%) | $2.4 \times 10^4$ (78.2%) | $4.8 \times 10^3$ (95.6%) | 100% |
| Sal. typhi | $3.2 \times 10^5$ | $2.8 \times 10^5$ (12.5%) | $2.1 \times 10^5$ (34.4%) | $1.0 \times 10^5$ (68.8%) | 99.7% |
| P. aeruginos | $4.8 \times 10^5$ | $4.6 \times 10^5$ (4.2%) | $4.2 \times 10^5$ (12.5%) | $3.8 \times 10^5$ (20.8%) | 70.8% |
| C. albicans | $3.4 \times 10^5$ | $3.4 \times 10^5$ (0.0%) | $3.4 \times 10^5$ (0.0%) | $3.3 \times 10^5$ (2.9%) | 0% |

2-3) Determination of bactericidal effect on *Bacillus* sp.

Bactericidal effect of *Lactobacillus paracasei* viro-01 of the present invention was measured versus *Bacillus*. The test strains used were *Bacillus cereus* and *Bacillus subtilis*, known as food poisoning bacteria. Seed cultures of the said test bacteria were smeared on nutrient agar media, incubated at 36° C. for 24 hours, and suspended in sterilized physiological saline solution. At this time, test solutions were diluted to $1.5 \times 10^8$ cfu/ml. The test solutions were serially diluted $10^2$, $10^3$, $10^4$ times and added, with an equal amount of the *Lactobacillus paracasei* viro-01 of the present invention, treated for 30 min, 1 hour, 6 hours and 24 hours, then added to nutrient agar and cultivated at 37° C. for 48 hours to observe growth. The said test solution to which the *Lactobacillus paracasei* viro-01 of the present invention was not added was used as a control group.

As shown in Table 3, numbers of test bacteria increased in the control group as time elapsed, but when the *Lactobacillus paracasei* viro-01 of the present invention was added, *bacillus* numbers decreased with time, and after 24 hours treated *bacillus* strains were completely killed. Thus, it was shown that the *Lactobacillus paracasei* viro-01 of the present invention had a strong bactericidal effect versus *bacillus* strains.

2-4) Antibiotic sensitivity

Antibiotic sensitivity of the *Lactobacillus paracasei* viro-01 of the present invention were tested. The antibiotic resistance test was carried out by Scientec Lab Center Co., Ltd.(Daejeon city, Daedeok, Korea) approved by the KFDA.

Antibiotics used were Cephalexin, Flumequine, Furazolidone, Gentamycin, Spectinomycin, Tetracycline, Tiamulin, Neomycin, Chloramphenicol and Kanamycin, and test procedures were as described below.

5 to 6 colonies of cultured *Lactobacillus paracasei* viro-01 were selected, inoculated into bacterial growth medium composed of peptone 10.0 g/L, beef extract 10.0 g/L, yeast extract 5.0 g/L, glucose 20.0 g/L, Tween 80 1.0 mL/L, $K_2HPO_4$ 2.0 g/L, sodium acetate 5.0 g/L, triammonium citrate 2.0 g/L, $MgSO_4 \cdot 7H_2O$ 0.2 g/L and $MnSO_4 \cdot 4H_2O$ 0.2 g/L and incubated at 37° C. Turbidity of said culture was adjusted to MacFarland No. 0.5, and used as test bacteria solution. Said test bacteria solution was smeared on Mueller Hinton agar plates and antibiotic sensitivity test disc was added thereto and incubated at 37° C. for 16 hours.

Antibiotic sensitivity was determined by measuring the area of growth inhibition surrounding each test disc.

Experimental results showed that *Lactobacillus paracasei* viro-01 of the present invention had resistance to Cephalexin, Flumequine, Furazolidone, Spectinomycin, and Kanamycin. Also, the said microorganism showed moderate resistance to Gentamycin and Neomycin. On the other hand, no resistance to Tetracycline, Tiamulin and Chloramphenicol was observed(Table 4).

TABLE 3

Bactericidal effect of the *Lactobacillus paracasei* viro-01
of the present invention versus *Bacillus cereus* and *Bacillus subtillis*

| | No. of *Bacillus cereus* (cfu/ml) | | | No. of *Bacillus subtilis* (cfu/ml) | | |
|---|---|---|---|---|---|---|
| treatment time | $10^2$* | $10^3$ | $10^4$ | $10^4$ | $10^3$ | $10^4$ |
| control | $4.8 \times 10^2$ | $9.3 \times 10^3$ | $4.3 \times 10^4$ | $2.9 \times 10^4$ | $4.8 \times 10^3$ | $8.7 \times 10^4$ |
| 30 min. treatment | $1.4 \times 10^2$ | $4.1 \times 10^3$ | $1.2 \times 10^4$ | $1.1 \times 10^2$ | $2.3 \times 10^3$ | $9.3 \times 10^3$ |
| 1 hr treatment | $4.6 \times 10^2$ | $2.3 \times 10^3$ | $4.9 \times 10^2$ | 291.8 | $1.1 \times 10^2$ | $1.0 \times 10^2$ |
| 6 hrs treatment | — | 12 | 13 | — | 9 | 12 |
| 24 hrs treatment | — | — | — | — | — | — |

*representing dilution times of test bacterial strain

TABLE 4

| | | Antibiotic-sensitivity test | | | | |
|---|---|---|---|---|---|---|
| | content | growth-inhibition zone (mm) | resistance | Interpretation of growth-inhibiting zone (mm) | | |
| Antibiotics | (μg/disc) | | | resistant | moderate | sensitive |
| sephalexin | 10 | 0 | strong | below 11 | 12~13 | above 14 |
| flumequine | 10 | 0 | strong | below 12 | 13~16 | above 17 |
| furazolidone | 10 | 0 | strong | below 11 | 11~13 | above 14 |
| gentamycin | 10 | 13 | moderate | below 12 | 13~14 | above 15 |
| spectinomycin | 10 | 0 | strong | below 11 | 12~13 | above 14 |
| tetracycline | 30 | 30 | none | below 14 | 15~18 | above 19 |
| tiamulin | 10 | 28 | none | below 11 | 12~13 | above 14 |
| neomycin | 10 | 13 | moderate | below 12 | 13~16 | above 17 |
| chloramphenicol | 30 | 30 | none | below 12 | 13~17 | above 18 |
| kanamycin | 10 | 9 | strong | below 13 | 14~17 | above 18 |

EXAMPLE 3

Production of lactic acid bacteria fruit juice fermentation liquid using *Lactobacillus paracasei* viro-01 of the present invention and safety test for the same Fermentation product was prepared using the *Lactobacillus paracasei* viro-01 of the present invention and it was examined for safety. Said fermentation product was prepared by inoculating the *Lactobacillus paracasei* viro-01 of the present invention into juice of ripened fruit and fermenting to produce lactic acid bacteria fruit juice fermentation liquid. *Lactobacillus paracasei* viro-01 of the present invention was inoculated into MRS broth, incubated at 37° C. for 48 hours, 2% of said *Lactobacillus paracasei* viro-01 was inoculated into mixed fruit juice composed of sterilized apple juice 50%, orange juice 20%, grape juice 20% and jujube juice 10% and then fermented anaerobically at 30° C. Said mixed fruit juice was diluted with purified water to Brix 5 to a brix degree of 5%. After 72 hours, when pH reached 3.0, said mixed fermentation juice was fermented at 30° C. for about 7 days until it became acidity of 4.0 with aeration for 1 hour every 24 hours.

Lactic acid bacteria fruit juice fermentation liquid of the present invention was tested for *E. coli* group, number of bacteria and tar pigment, based on the general test method of Food Industry(notice of 2000-18, Korean Food & Drug Administration). As a result, said fermentation liquid was given judgement of suitability as food sauces from Korea Food & Drug Administration since it met the criteria which requires foodstuffs to have the following conditions: having unique color selectiveness and having not abnormal taste and odor, being *E. coli* group negative, tar pigment being not detected, and being suitable for preservative standard), and harmful remaining materials(Pb, Cd, Hg, As, Cr16) were not detected.

EXAMPLE 4

Production of lactic acid bacteria fruit juice re-fermentation liquid using *Lactobacillus paracasei* viro-01 of the present invention.

Lactic acid bacteria fruit juice fermentation liquid of the above example 3 was recovered and remaining bacterial mass and precipitates were used for re-fermenting *Lactobacillus paracasei* viro-01 of the present invention. Purified water was added to the remaining bacterial mass and precipitates to dilute them 5 times, and anaerobically fermented at 30° C. After 72 hours, when pH reached 3.0, they were fermented at 30° C. for about 7 days until acidity became 4.0, while aerating for 1 hour every 24 hours. On completion of fermentation, purified water was added to the fermentation liquid to dilute it 5 times, and aged.

EXAMPLE 5

Effect of *Lactobacillus paracasei* viro-01 of the present invention on diarrhea prevention and weight gain of parent and progeny pigs.

The present inventors investigated the effect of *Lactobacillus paracasei* viro-01 of the present invention on diarrhea prevention and growth of parent and progeny pigs. At a breeding farm in Ansung, Korea, 3 groups of 3 parent pigs and 30 progeny pigs were grouped and the present fermentation liquid was orally administered for 2 days to 10 days or more. At this time, to the first group was administered fermentation liquid of the present invention for 10 days and from day 10, drinking water having 0.2% of said fermentation liquid added was administered.

The second group was administered with physiological solution for 2 to 10 days or more, and from day 10, was administered with drinking water having 2% of physiological solution added. The third group was administered physiological solution for 2 to 10 days or more and from day 10, was only regular feed and water administered(Table 5). Death rate, diarrhea incidence, and weight gain for the said experimental groups were examined.

TABLE 5

Experimental group and dosage of fermentation liquid

| test group | No. of parent pig | No. of progeny pig | dosage | | | | | | | | | remarks |
|---|---|---|---|---|---|---|---|---|---|---|---|---|
| | | | day 2 | day 3 | day 4 | day 5 | day 6 | day 7 | day 8 | day 9 | After day 10 | |
| 1 | 3 | 30 | 2 ml | 2 ml | 3 ml | 3 ml | 5 ml | 5 ml | 7 ml | 7 ml | 10 ml | Fermentation liquid administered (ml), 10 days later drinking water administered(0.2%) |
| 2 | 3 | 30 | 2 ml | 2 ml | 3 ml | 3 ml | 5 ml | 5 ml | 7 ml | 7 ml | 10 ml | physiological saline orally administered(ml), drinking water administered(0.2%) |
| 3 | 3 | 30 | 2 ml | 2 ml | 3 ml | 3 ml | 5 ml | 5 ml | 7 ml | 7 ml | 10 ml | physiological saline orally administered(ml), 10 days later, not administered |

As an experimental result showed that upon occurrence of a premature diarrhea and a feeding diarrhea due to feed supplying to weaned piglet, administration of the present fermentation liquid decreased the death rate of animal by 6.6%, and also decreased diarrhea incidence by about 53 to 87%. Growth rate of animal also increased by 5.9%. Thus, it was confirmed that there were decrease of death rate due to diarrhea and decrease of diarrhea incidence, and effect of individual growth, when the present lactic acid bacteria fermentation liquid was administered to suckling pigs and weaned progeny pigs by means of drinking water containing 0.2% of said liquid. Also it can be seen that administration of 0.1 to 0.2% of the present lactic acid bacteria fermentation liquid-containing drinking water has contributed to improvement of productivity in farm.

the treatment group to which the present lactic acid bacteria fermentation liquid was supplied and the treatment group to which antibiotic was supplied, compared to the control group, and numbers of beneficial bacteria increased significantly in the treatment group to which the present lactic acid bacteria fermentation liquid was supplied. *Salmonella* was not detected in appendix of animal known as microorganism reservoir, and *E. coli* was not present in the antibiotic treatment group and was found to be low in the treatment group to which the present lactic acid bacteria fermentation liquid was supplied, compared to control group. The number of lactic acid bacteria in appendixes of animals increased in the treatment group to which the present lactic acid bacteria fermentation liquid was supplied(Table 6)

TABLE 6

Determination of the changes in intestinal flora in weaned progeny pigs to which lactic acid bacteria fermentation liquid of the present invention was supplied.

| treatment group (%) | Ileum (CFU) | | | | Appendix(CFU) | | | |
|---|---|---|---|---|---|---|---|---|
| | Salmonella | E. coli | Yeast | Lactobacillus | Salmonella | E. coli | Yeast | Lactobacillus |
| control | $2.0 \times 10^3$ | $1.0 \times 10^4$ | $2.3 \times 10^4$ | $1.2 \times 10^4$ | 0 | $5.0 \times 10^4$ | $3.0 \times 10^4$ | $1.1 \times 10^5$ |
| antibiotic 0.1 | 0 | $3.0 \times 10^3$ | $1.8 \times 10^4$ | $1.8 \times 10^4$ | 0 | 0 | 0 | $4.7 \times 10^5$ |
| fermentation liquid 0.1 | $1.0 \times 10^3$ | $6.0 \times 10^3$ | $3.0 \times 10^3$ | $2.5 \times 10^5$ | 0 | $2.0 \times 10^3$ | $1.0 \times 10^4$ | $6.0 \times 10^5$ |

EXAMPLE 6

Determination of changes in intestinal flora in weaned progeny pigs to which fermentation liquid of *Lactobacillus paracasei* viro-01 according to the present invention was supplied.

In order to study the changes of intestinal flora in weaned progeny pigs by supplying lactic acid bacteria fermentation liquid of the present invention, spot breeding test was performed at Chonbuk University in Korea. The test comprised establishing a control group to which the present lactic acid bacteria fermentation liquid was not supplied, a treatment group to which 0.1% of commercial antibiotic was supplied and a treatment group to which drinking water containing 0.1% of the present lactic acid bacteria fermentation liquid was supplied, respectively, and assigning 12 animals including 6 males and 6 females to each treatment group. The test period was 8 weeks.

As a result, numbers of the pathogenic microorganism, *Salmonella* and *E. coli* in the ileum of animals decreased in

EXAMPLE 7

Test of deodorizing capacity for the deodorizing composition of the present invention Lactic acid bacteria fermentation liquid of the present invention was diluted with purified water 150 times and investigated for the degree of removing offensive odor in a deodorizing test apparatus. As offensive odor source there were used silver methylmercaptan 50 ppm, ammonia 60 ppm, trimethylamine 60 ppm, and hydrogen sulfide 60 ppm, which were injected to the deodorizing test apparatus while controlling concentrations of the offensive odors with gastec.

Lactic acid bacteria fermentation liquid of the present invention was diluted 150 times, and 20 ml of the said liquid was sprayed through the sprayer and concentrations of odors determined after 30 min, 1 hour and 6 hours.

As a result, after 6 hours, deodorizing power versus basic odorant materials, ammonia and trimethylamine displayed removal rate of respective 85% and 80% compared to initial concentration, and after 6 hours, deodorizing power for acidic odorant materials, methylmercaptan and hydrogen sulfide displayed removal rate of respective 24% and 47% compared to initial concentration(Table 7).

TABLE 7

Deodorizing capacity of the deodorizing composition of the present invention.

| odorous material | Initial | 30 min | 1 hr | 6 hrs |
|---|---|---|---|---|
| ammonia | 60 | 19 | 18 | 9 |
| trimethylamine | 60 | 28 | 26 | 12 |
| methylmercaptane | 50 | 45 | 45 | 38 |
| hydorgen sulfide | 60 | 40 | 40 | 32 |

EXAMPLE 8

Meat softening and deodorizing effect of lactic acid bacteria fermentation liquid of the present invention in meat and fish.

Reduction effect of offensive odor and meat softening effects when natural lactic acid bacteria food additive prepared from lactic acid bacteria fermentation liquid of the present invention was added to meat and fish cooking were tested.

Food additive of the present invention was lactic acid bacteria fermentation liquid of the present invention diluted with purified water 50 times. This additive was added to steamed pig rib, panbroiled pork, broiled beef, steamed beef rib, chicken broth, fried chicken, broiled mackerel, spiced fish soup and Kimchi pot stew, and the smell, toughness and taste were rated on a scale of 0 to 10. Results were statistically treated by using dispersion analysis and Duncan's Multiple range test and examined for significance. At this time, for comparison, a control material of commercially available refined rice wine was used. Amount of natural seasoning food of the present invention and refined rice wine was 2 big spoonfuls based on total of 500 g of both said meat and fish. First, meat and fish were mixed with lactic acid bacteria seasoning food or refined rice wine and then subsequent cooking steps were performed.

As a result, food additive of the present invention was superior to refined rice wine at removing order of in meat and fish. For meat-softening action and taste, it was also confirmed that food additive of the present invention played the role of excellent natural seasonings(Table 8A–8C).

TABLE 8a

Meat softening and deodorizing effect on meat and fish

| | steamed pork rib | | | panbroiled pork | | | broiled beef | | |
|---|---|---|---|---|---|---|---|---|---|
| | odor | toughness | taste | odor | toughness | taste | odor | toughness | taste |
| 1 | $1.650^c$ | $1.9625^b$ | $7.7375^a$ | $1.1250^b$ | $0.9375^b$ | $7.7125^a$ | $2.3125^b$ | $2.8375^b$ | $7.6250^a$ |
| 2 | $2.5875^b$ | $2.4125^b$ | $7.4500^a$ | $1.7875^b$ | $1.1375^b$ | $7.6000^a$ | $2.3250^b$ | $2.9875^b$ | $7.0500^a$ |
| 3 | $5.2125^a$ | $5.0875^a$ | $5.2250^b$ | $3.4250^a$ | $3.8500^a$ | $5.9875^b$ | $4.3375^a$ | $4.7375^c$ | $5.5250b$ |
| F value | 81.41 | 59.96 | 28.64 | 16.68 | 82.38 | 39.74 | 23.14 | 10.30 | 14.62 |
| Significance | *** | *** | *** | *** | *** | *** | *** | *** | *** |

TABLE 8b

Meat softening and deodorizing effect on meat and fish

| | steamed beef rib | | | chicken broth | | | fried chicken | | |
|---|---|---|---|---|---|---|---|---|---|
| | odor | toughness | taste | odor | toughness | taste | odor | toughness | taste |
| 1 | $1.1875^c$ | $1.8875^c$ | $8.11255^a$ | $1.4375^c$ | $2.2250^b$ | $7.7125^a$ | $1.2500^b$ | $2.125^b$ | $8.2625^a$ |
| 2 | $1.8000^b$ | $2.4125^b$ | $7.7625^a$ | $2.1125^b$ | $2.2875^b$ | $7.2250^a$ | $1.7000^b$ | $2.2652^b$ | $7.4000^a$ |
| 3 | $3.0125^a$ | $3.3625^a$ | $6.0250^b$ | $4.3875^a$ | $3.7375^a$ | $5.3375^b$ | $3.6375^a$ | $4.1375^a$ | $6.1000^b$ |
| F value | 22.37 | 22.92 | 16.62 | 55.16 | 10.87 | 36.40 | 31.74 | 14.98 | 13.29 |
| Significance | *** | *** | *** | *** | *** | *** | *** | *** | *** |

TABLE 8c

Meat softening and deodorizing effect on meat and fish

| | broiled mackerel | | | spiced fish soup | | Kimchi pot stew | |
|---|---|---|---|---|---|---|---|
| | odor | hardness | taste | odor | taste | odor | taste |
| 1 | $1.2125^c$ | $1.5125^a$ | $7.9875^a$ | $1.6000^b$ | $8.1500^a$ | $1.8875^b$ | $8.5375^a$ |
| 2 | $2.2750^b$ | $1.4500^a$ | $7.9250^a$ | $1.9250^b$ | $7.8875^b$ | $2.0375^b$ | $7.8000^b$ |
| 3 | $3.5125^a$ | $1.8000^a$ | $7.2000^b$ | $3.3625^a$ | $6.3125^b$ | $4.5750^a$ | $6.3125^c$ |
| F value | 29.87 | 1.41 | 4.36 | 16.29 | 26.43 | 44.33 | 22.00 |
| Significance | *** | | * | *** | *** | *** | *** |

1) 1: food additive of the present invention added, 2: refined rice wine added, 3: control group
2) Duncan's multiple range test: comparing each sample at a given property value, thereby being considered significance($p < 0.05$) if not the same alphabetic symbol.
3) significance: ***; significant ($p < 0.001$), *: significant ($p < 0.1$)

The invention claimed is:

1. A purified culture of *Lactobacillus paracasei* viro-01 (KCTC 10132BP).

2. Fermentation liquid comprising a purified culture of *Lactobacillus paracasei* viro-01 (KCTC 10132BP).

3. A probiotic composition treating intestinal diseases of animals, comprising a purified culture of *Lactobacillus paracasei* viro-01(KCTC 10132BP) or fermentation liquid thereof.

4. The probiotic composition of claim 3, wherein the said intestinal disease is infectious diarrhea caused by pathogenic microorganisms, gastroenteritis, inflammatory intestinal disease, neurological intestinitis syndrome, overgrowth of small intestinal microorganisms and intestinal feeding diarrhea.

5. A feed additive comprising a purified culture of *Lactobacillus paracasei* viro-01(KCTC 10132BP) or fermentation liquid thereof.

6. A deodorizing agent comprising a purified culture of *Lactobacillus paracasei* viro-01 (KCTC 10132BP) or fermentation liquid thereof.

7. A food composition comprising a purified culture of *Lactobacillus paracasei* viro-01(KCTC 10132BP) or fermentation liquid thereof.

8. A method for preparing fermentation liquid of *Lactobacillus paracasei* viro-01(KCTC 10132BP) comprising (a) inoculating *Lactobacillus paracasei* viro-01(KCTC 10132BP) into fruit juice;

(b) anaerobically fermenting the *Lactobacillus* at 15 to 45° C.; and (c) then fermenting the *Lactobacillus* at 20 to 40° C. with aeration until the pH decreases to a value of 2.0 to 5.0.

9. The method of claim 8, further comprising (a) recovering the fermentation liquid produced after step (c) in claim 9;

(b) adding purified water to the remaining *Lactobacillus paracasei* viro-01(KCTC 10132BP) bacterial mass and precipitates to dilute them 1 to 10-fold;

(c) re-fermenting the bacterial mass and precipitates of step (b); and (d) adding purified water to the re-fermented bacterial mass and precipitates of step (c) to dilute them 1 to 10-fold.

* * * * *